(12) United States Patent
Shields et al.

(10) Patent No.: US 6,417,498 B1
(45) Date of Patent: Jul. 9, 2002

(54) NEONATAL SUBSTRATE WARMER

(76) Inventors: Janice M. Shields; Paul W. Shields, both of 39410 Ladrone Ct., Sterling Heights, MI (US) 48313

( * ) Notice: Subject to any disclaimer, the term of this patent is extended or adjusted under 35 U.S.C. 154(b) by 0 days.

(21) Appl. No.: 09/834,124

(22) Filed: Apr. 12, 2001

(51) Int. Cl.[7] .......................... A47J 27/10; A47J 36/26; A47J 41/00

(52) U.S. Cl. ................... 219/521; 219/386; 219/428; 219/430; 219/432; 219/433; 222/146.5

(58) Field of Search ................... 219/386, 218, 219/428, 430, 432, 433; 222/146.5

(56) References Cited

U.S. PATENT DOCUMENTS

| | | | |
|---|---|---|---|
| 111,476 A | 1/1871 | Ronning | |
| 290,519 A | 12/1883 | Brandenburg | |
| 1,416,914 A | 5/1922 | Vickery | |
| 1,625,002 A | 4/1927 | Wagner | |
| 1,662,399 A | 3/1928 | Rood et al. | |
| 1,759,723 A | 5/1930 | Weld | |
| 1,816,698 A | 7/1931 | Replogle | |
| 1,851,512 A | 3/1932 | Hinkley | |
| 2,060,155 A | 11/1936 | Wilhelm | |
| 2,413,176 A | 12/1946 | Deaton | |
| 2,428,996 A * | 10/1947 | Schworm | 219/438 |
| 2,513,577 A | 7/1950 | Malme | |
| 2,541,218 A * | 2/1951 | Doerr | 219/521 |
| 2,551,651 A * | 5/1951 | Vandewater | 392/441 |
| 2,584,435 A * | 2/1952 | Doerr | 219/218 |
| 2,647,653 A | 8/1953 | Dube | |
| 2,843,719 A * | 7/1958 | Smith et al. | 219/429 |
| 2,853,205 A * | 9/1958 | Boyd | 219/218 |
| 3,082,900 A | 3/1963 | Goodman | |
| 3,432,641 A * | 3/1969 | Welke | 219/433 |
| 3,778,594 A * | 12/1973 | Wightman | 219/432 |
| 3,804,076 A | 4/1974 | Fant et al. | |
| 3,892,945 A * | 7/1975 | Lerner | 219/432 |
| 3,896,973 A * | 7/1975 | Morgan | 222/146.5 |
| 3,984,656 A * | 10/1976 | Morgan | 219/439 |
| 4,007,367 A | 2/1977 | Rusteberg et al. | |
| 4,107,513 A * | 8/1978 | Ashford | 219/521 |
| 4,256,697 A | 3/1981 | Baldwin | |
| 4,561,563 A | 12/1985 | Woods | |
| 4,597,435 A | 7/1986 | Fosco, Jr. | |
| 4,782,670 A | 11/1988 | Long et al. | |
| 5,073,697 A | 12/1991 | Uchiyama | |
| 5,229,580 A | 7/1993 | Chioniere | |
| 5,248,870 A | 9/1993 | Redal | |
| 5,551,592 A | 9/1996 | Barton et al. | |
| 5,653,343 A | 8/1997 | Imai | |
| 5,808,276 A * | 9/1998 | Padilla | 219/386 |
| 5,810,196 A | 9/1998 | Lundy | |
| 5,924,303 A | 7/1999 | Hodosh | |
| 5,975,337 A | 11/1999 | Hadley | |

FOREIGN PATENT DOCUMENTS

| | | | |
|---|---|---|---|
| EP | 181535 | * | 5/1986 |
| JP | 9-238831 | * | 9/1997 |

\* cited by examiner

*Primary Examiner*—Joseph Pelham
(74) *Attorney, Agent, or Firm*—Vanophem & Vanophem, P.C.

(57) ABSTRACT

A receptacle-type heating device for automatically warming and vibrating a multitude of containers simultaneously in order to thaw, warm, and mix cold or frozen liquid in an expedient and accurate manner. The device heats each container to a desired temperature using heat exchange of heated water with the container. The device includes a heater block having multiple wells therein, and removable reservoirs disposed respectively within the wells for receiving the water. Heating elements are disposed between the removable reservoirs and the heater block within the wells for heating the removable reservoirs, the water, and the containers placed therein. The container typically is a baby bottle, syringe, test tube, or the like.

18 Claims, 3 Drawing Sheets

NEONATAL SUBSTRATE WARMER

CROSS-REFERENCES TO RELATED APPLICATIONS

Not applicable.

FEDERALLY SPONSORED RESEARCH OR DEVELOPMENT

Not applicable.

REFERENCE TO A MICROFICHE APPENDIX

Not applicable.

BACKGROUND OF THE INVENTION

1. Field of the Invention

The present invention generally relates to receptacle devices used to heat fluid bearing containers. More specifically, this invention relates to a novel receptacle-type heating device for warming baby bottles containing breast milk in a quick, reliable, and automated manner.

2. Description of the Related Art

In general, devices for warming fluid containers have been used extensively in the prior art. Until now, however, there have been no such devices suitable for use in warming baby bottles in neonatal intensive care units (NICU) of a hospital. NICU are responsible, among many other things, for administering substrate, formula, or breast milk to newborn infants. Recent medical studies reinforce the fact that newborns benefit significantly from receiving colostrum—the first milk of the mother after giving birth. Colostrum is known to supply extremely high concentrations of antibodies essential to the development of a newborn's immune system, and is also thought to aid in establishing digestion of the newborn. Accordingly, it is absolutely critical to capture the colostrum from the mother and carefully preserve it for later administration to the newborn as quickly, cleanly, and safely as possible.

In current practice, NICU nurses capture breast milk from the mother in baby bottles, refrigerate or freeze the breast milk, rewarm the breast milk, and feed it to the newborn. Newborns tend to feed about eight times per day, which necessitates frequent thawing, warming, and administering of breast milk. This frequent and time consuming process wastes an enormous amount of time for the NICU nurses, especially due to the manually intensive method of thawing and warming the breast milk. Using a microwave to warm the breast milk is not a viable option since such a process has a detrimental effect on the quality of the breast milk.

Instead, the breast milk is thawed and warmed by placing the baby bottle into a large insulated cup full of hot tap water. Due to simple heat transfer principles, the hot water quickly cools down even before the breast milk has had a chance to thaw, much less warm up to body temperature. Therefore, NICU nurses must repeatedly add hot water to the insulated cup in order to thaw and warm the breast milk. As such, NICU nurses waste precious time maintaining an archaic warming process instead of attending to newborns. In the alternative, NICU nurses sometimes leave the insulated cup and baby bottle under a faucet of running hot water. Unfortunately, this approach works, for only one bottle at a time and, if left unattended, results in a temporary depletion of hot water supply or possibly overheated breast milk.

There are other problems with the insulated cup warming process. For one, since the method is entirely manual and subjective, it is possible that the temperature of the breast milk is inadequately warmed and is either too cold or too hot. Additionally, it is important that the bottle be shaken to agitate and properly mix the breast milk; however, because of the often hurried pace of an NICU and the manual nature of the warming process the baby bottles are not always adequately shaken. Finally, the current warming process results in a mess of half full insulated cups lying about on NICU counter tops that often times are inadvertently knocked over, creating an even bigger mess and an aura of untidiness.

The prior art has suggested use of heated bath immersion devices. For example, one complicated apparatus in effect accomplishes the same result as the insulated cup/running tap water process mentioned above. U.S. Pat. No. 4,597,435 to Fosco, Jr. teaches a bottle warmer that uses a thermal transfer fluid to heat a baby feeding bottle. Fosco, Jr. discloses a portable device having an open top cup-like container for holding hot water therein. A removable platform is positioned within the container for suspending a baby bottle inside the container in contact with the hot water. The removable platform separates the container into an upper and lower chamber. An open-ended tube extends from the top of the container down into the lower chamber for conveying incoming tap water thereto. Accordingly, the portable device is placed under a faucet dispensing running hot water such that the hot water is directed down into the open-ended tube. The hot water thus enters the lower chamber and is forced under pressure up around the sides of the suspended baby bottle and into the upper chamber until it exits via the open top of the container. Obviously, the Fosco, Jr. warmer provides an unnecessarily complex apparatus for bottle warming that, in effect, is substantially similar to the insulated cup method that NICU nurses currently use. Therefore, Fosco, Jr. does not address, much less solve, the above-mentioned problems. Furthermore, the background section of Fosco, Jr. discusses the shortcomings of several other receptacle-type devices that need not be further explored here.

Additionally, the prior art has suggested use of dry block heaters for heating test tubes. Dry block designs typically use metal blocks having a central or localized heating passage therethrough. A series of tube wells are typically arranged in a pattern within the metal block in close proximity to the heating passage. Heat flowing through the heating passage transfers through the block, into the tube wells, and into test tubes placed in the tube wells. This design has one significant drawback in particular. The tube wells are of a necessarily fixed diameter to accept a slightly undersized test tube, thereby establishing a close fitting relationship between the metal block and test tubes to enable effective heat transfer therebetween. Unfortunately, this configuration is not flexible enough to permit use of a variety of sizes of test tubes with a particular block. Therefore, only one size of test tube, or baby bottle, could be used with such a device. Since different NICU inevitably use bottles from different manufacturers that are of different sizes and shapes, this type of fixed block design is not practical for the purposes intended according to the present invention.

From the above, it can be appreciated that baby bottle warming methods and apparatus of the prior art are not fully optimized. Therefore, what is needed is an automatic bottle-heating device that quickly, accurately, individually, and simultaneously warms and vibrates a multitude of baby bottles so as to adequately heat and mix breast milk contained therein.

BRIEF SUMMARY OF THE INVENTION

According to the preferred embodiment of the present invention, there is provided a device for warming and vibrating a multitude of baby bottles simultaneously in order to thaw, warm, and mix refrigerated breast milk in an expedient and accurate manner. The device heats each baby bottle to a desired temperature using heat exchange of water with the baby bottle. The device includes a heater block having several wells therein. Several removable reservoirs for receiving the water are disposed respectively within the wells of the heater block. Several heating elements are provided for heating the removable reservoirs and the water contained therein. The heating elements are disposed respectively between the removable reservoirs and the heater block within the wells of the heater block.

In operation, the device is plugged into a standard wall socket and is switched on with a master switch. Each heating element is individually activated by throwing its own dedicated switch. Current thereby flows from the wall socket to the heating element thus causing heat to emanate therefrom. The heat flows easily through each removable reservoir, through the water contained therein, through the baby bottle, and into the breast milk. Optionally, the heating device can be mounted atop a vibrator device that is used to agitate and mix the breast milk.

It is an object of the present invention to provide a heating device that when compared to using hot tap water, more quickly, cleanly, and accurately thaws and warms liquid inside of a container.

It is another object to provide a heating device that does not require use of hot tap water and that warms liquid inside of a container to a predetermined temperature without overheating the liquid.

It is still another object to provide a heating device that automatically agitates and mixes liquid inside of a container.

It is yet another object to provide a heating device that accommodates a range of sizes of containers to be heated.

It is a further object to provide a heating device that is capable of warming a multitude of containers individually and simultaneously.

It is still a further object to provide a heating device that accomplishes the above-mentioned objectives using a unique receptacle design configuration by incorporating certain features of well-known consumer household appliances such as heating elements of toaster ovens and thermostatic circuits of coffee makers.

It is yet a further object to provide a heating device for heating baby bottles, syringes, test tubes, and the like.

These objects and other features, aspects, and advantages of this invention will be more apparent after a reading of the following detailed description and appended claims taken in conjunction with the accompanying drawings.

DETAILED DESCRIPTION OF THE PREFERRED EMBODIMENT

Figure 1A:
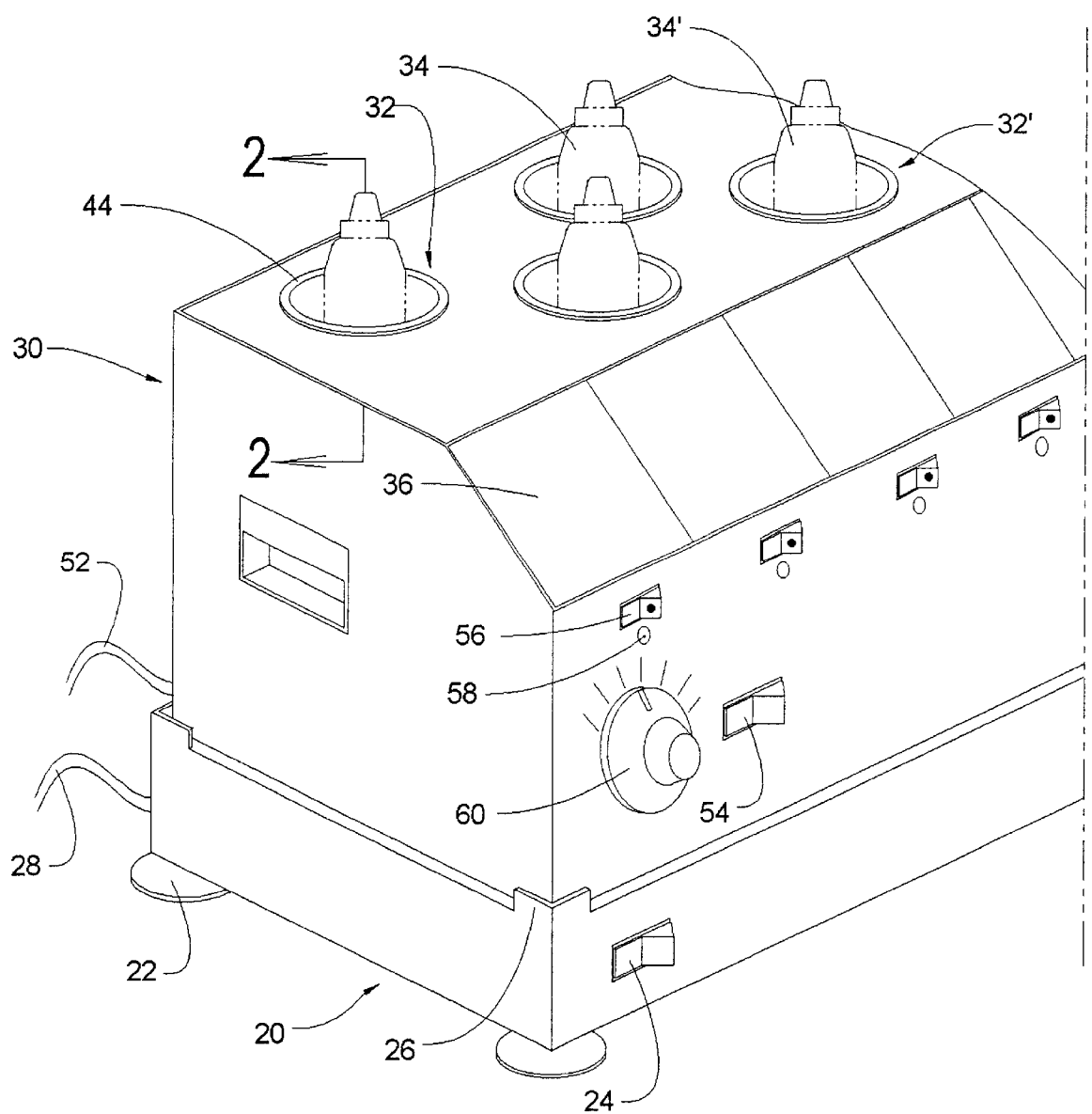
FIG. 1A is a partial perspective view of a heating device according to the preferred embodiment of the present invention.
Figure 1B:
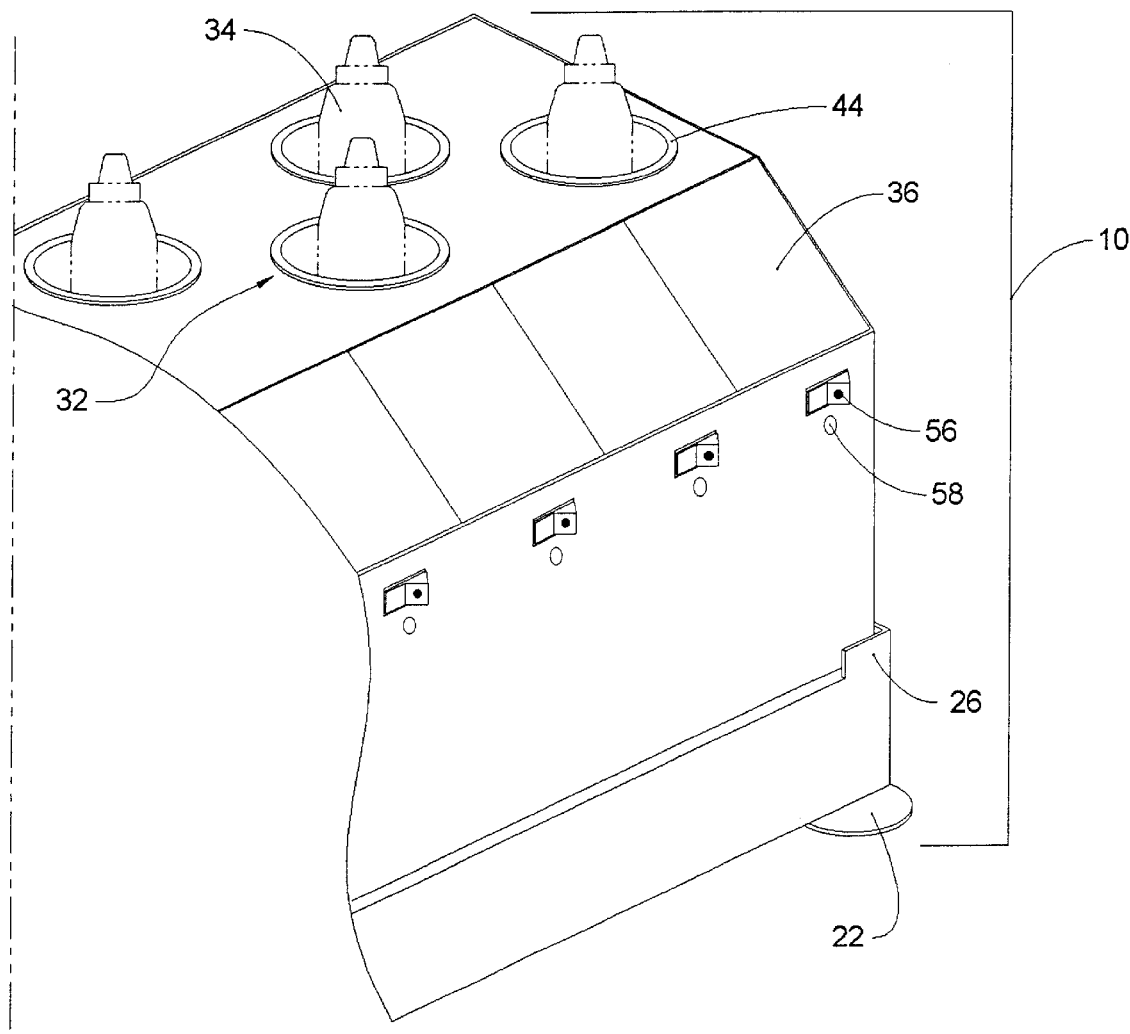
FIG. 1B is the rest of the partial perspective view of the heating device of FIG. 1A.

Referring now in detail to the Figures, there is shown in FIGS. 1A and 1B a heating device 10 according to the preferred embodiment of the present invention. The heating device 10 generally includes a shaker or vibrator 20 and a heater block 30 mounted thereto.

The vibrator 20 is of a generally flat, rectangular shape and has suction cup feet 22 rendering the vibrator 20 suitable for use on a counter top. The vibrator includes a switch 24, a power cord 28, and raised corners 26 for retaining an item thereto. In general, similar such devices are typically found in chemistry laboratories, are well known in the art, and are readily available from Amerex Instruments, Inc. and Jepson Bolton, Inc., for example.

The heater block 30 is mounted to the vibrator 20 within the confines of the raised corners 26. The heater block 30 is also preferably rectangular and is preferably composed of an insulative type of material such as cork, synthetic cork, or a thermoset polymer. Alternatively, the heater block 30 can be composed of a thermoplastic or ceramic material. The heater block 30 is manufactured preferably by cutting a block of cork from raw stock and machining necessary features therein. Alternatively, a synthetic cork or thermoset polymer material can be molded to the desired shape and features of the heater block 30. The heater block 30 preferably includes eight heating chambers 32 but may include any number of heating chambers 32 for warming fluid-bearing containers therein, such as baby bottles 34. It is preferable to use individual isolated heating chambers 32, instead of one large bath, to avoid cross-communication of contaminants found on the exterior of the bottles 34. The heating chambers 32 are preferably sized to accommodate 2 oz. to 8 oz. baby bottles. It is important to accommodate the small 2 oz. baby bottle 34 to conserve on the precious breast milk contents thereof. It is contemplated that the heater block 30 could also be used to warm syringes, test tubes, or any other type of container. A display surface 36 of the heater block 30 is preferably composed of a "dry-erase" style marking surface to permit identification of each baby bottle 34.

Figure 2:
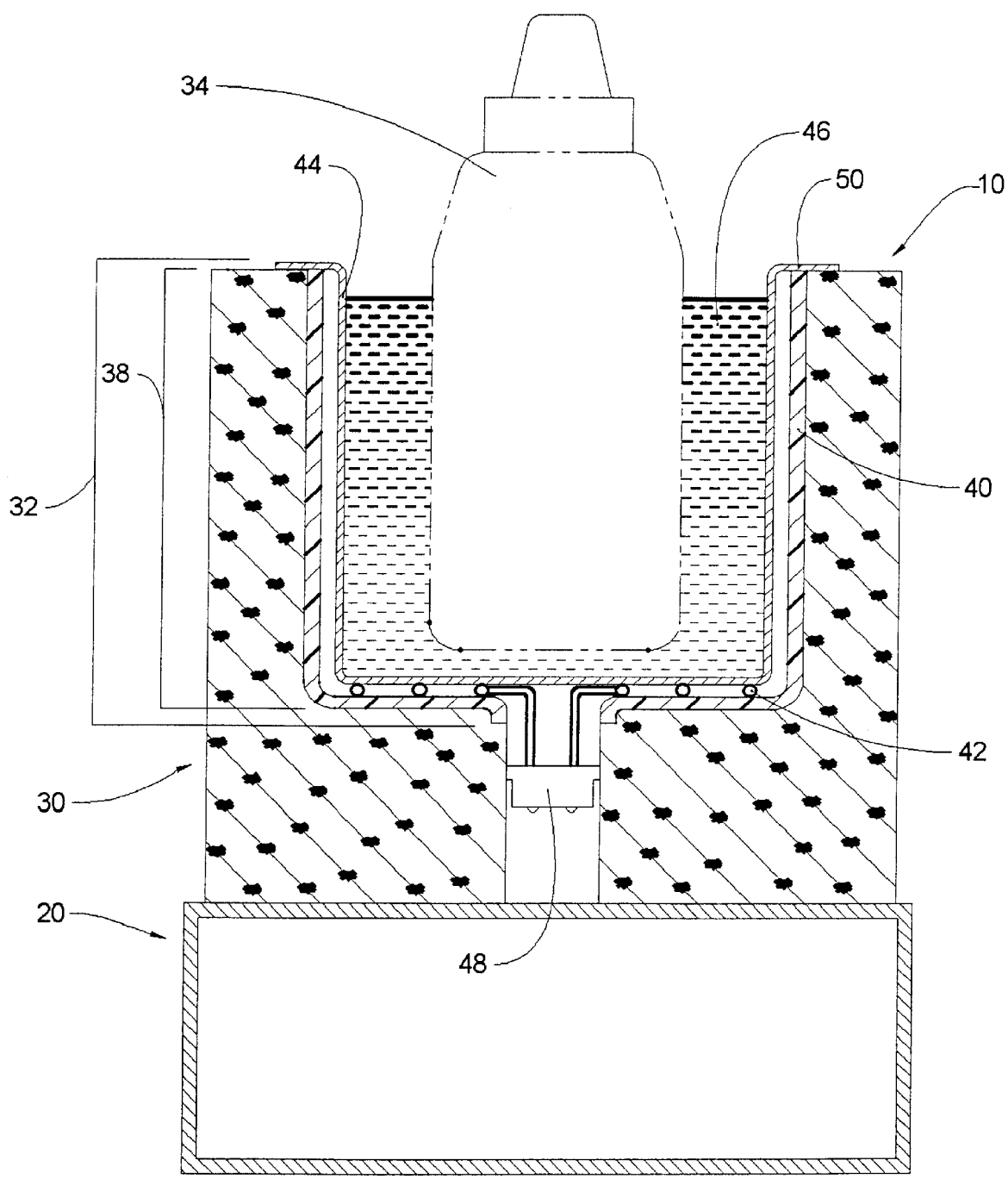
FIG. 2 is a partial cross-sectional view of the heating device of FIG. 1 illustrating a baby bottle disposed within a heating chamber of a heater block.

Referring now to FIG. 2, there is shown in cross section one of the eight heating chambers 32. The heating chamber 32 is defined primarily by a void or well 38 that is machined or formed in the heater block 30. Additionally, the heating chamber 32 includes a sleeve 40, a heating element 42, and a removable reservoir 44 filled with a heat-conducting medium, such as water 46.

The sleeve 40 is preferably made from stainless steel or a thermoset polymer and is inserted into the well 38 of the heater block 30 to protect the material of the heater block 30 from the heat effects of the heating element 42. Where the heater block 30 is made from a thermoset polymer having heat resistant properties, the sleeve 40 is not necessary and may be eliminated.

The heating element 42 is preferably a rigid resistor coil wound in a spiral pattern about an inside bottom portion of the sleeve 40 or directly inside the well 38 if the sleeve 40 is not used. The heating element 42 is similar to those found on stove top ranges or toaster ovens in a household kitchen, and is similarly water resistant. Alternatively, the heating element 42 could be flexible, similar to those found in a household toaster. A wire connector 48 connects to the heating element 42 to supply electricity thereto, as will be discussed hereinafter. In the alternative, it is contemplated that a gas fired heat supply could replace the electrical heating element 42.

The removable reservoir 44 is preferably made from food-grade stainless steel and is inserted atop the heating element 42. The removable reservoir 44 may be removed to enable easier cleaning thereof and to provide access to the heating element 42 for replacement or repair. An annular flange 50 locates the removable reservoir 44 relative to the heater block 30 and provides a splash guard feature to prevent water from reaching the heating element 42. The shape of the removable reservoir 44 is preferably cylindrical as shown, but may be in the shape of a conical flask to mitigate spillage of liquid therefrom during vibration or shaking. The removable reservoir 44 includes a predetermined volume of heat conducting media therein, such as the water 46. The water 46 is filled approximately half-way such that the water 46 does not overflow out of the removable reservoir 44 when the baby bottle 34 is inserted therein. Alternatively, any other heat conducting medium may be used such as an organic liquid, silicone gel, a powder, or glass shot.

The bottle 34 is preferably a 2 oz. baby bottle, but the heating device 10 should also accommodate up to an 8 oz. baby bottle. The bottle 34 may include a temperature sensor thereon that alerts a caregiver when a predetermined desired breast milk temperature has been reached. Preferably, however, a temperature sensing device is built in to the heating device 10 itself as will be described in more detail below.

Referring again to FIGS. 1A and 1B, the heater block 30 derives power from a standard 120 volt power outlet (not shown) via a standard power cord 52. The power cord 52 is connected to a main switch 54 that, in turn, is wired to each of eight heating chamber switches 56 that are in turn wired to respective heating elements 42. The main switch 54 and heating chamber switches 56 are preferably rocker style switches having indicator dots (not shown) thereon for indicating when the switch is on and the heating element shown in FIG. 2 is energized. Those skilled in the art will appreciate that standard wiring practices can be employed to connect the main switch 54 to the heating chamber switches 56 and the heating chamber switches 56 to each respective wire connector 48.

When the main switch 54 is on, and the heating chamber switch 56 on, current passes to the heating element 42 of FIG. 2. Referring again to FIG. 2, the heating element 42 supplies heat to the removable reservoir 44. Because the removable reservoir 44 is composed of thin steel and is, therefore, a good conductor, the removable reservoir 44 readily conducts heat from the heating element 42 into the water 46. The water 46 quickly warms up to approximately human body temperature or slightly thereover. Accordingly, the water 46 supplies heat to the baby bottle 34 disposed within the well 38 of the heater block 30 to thaw or warm the contents thereof. In order to more quickly heat and thoroughly mix the contents of the baby bottle 34, it is preferable to activate the vibrator 20 to mildly vibrate or shake the contents of the baby bottles 34. The vibration keeps the milk fat in solution with the rest of the substrate and thereby prevents separation of the substrate. The vibration also mixes different types of additives that can be added to a formula or breast milk. As mentioned above, according to the preferred embodiment of the present invention, the vibrator 20 is separate from the heater block 30, but it will be apparent to those skilled in the art that it can also be integrated with the heater block 30 if desired.

Referring again to FIGS. 1A and 1B, it is preferable that the heating device 10 include a built-in thermostat 60 to detect when the fluid temperature has stabilized at the desired level. This also ensures that the milk is thoroughly thawed, warmed, but not overheated, and thus provides sufficiently warm breast milk without the risk of burning the newborn. The thermostat 60 outputs to a light emitting diode 58 that glows or flashes when the desired temperature has been achieved and preferably includes an "auto shutoff" timer feature that cuts power to the heating element 42 after a predetermined time interval, such as a half hour.

Such thermostats 60 and related circuitry are well known in the art and are exemplified by similar devices commonly found in consumer coffee makers. As such, a thermostat circuit preferably includes a solid-state temperature sensor (not shown) that interrupts current when the heating element 42 reaches a certain predetermined temperature. When the temperature sensor cools down, it then reestablishes current flow to the heating element 42. By cycling on and off in this manner, the temperature sensor will maintain the heating element 42 at an even, predetermined temperature. One skilled in the art will recognize that selection of the temperature sensor is dependent upon the desired predetermined temperature of the heating element 42 as well as the thermodynamic capacity of the heating chamber 32. In other words, a large heating chamber holding a large volume of water will need a larger capacity temperature sensor than a smaller heating chamber holding a smaller volume of water. Additionally, a thermal fuse (not shown) can be connected between the heating element 42 and the heating chamber switch 56 of FIGS. 1A and 1B as a safety feature to interrupt current flow in the event of significant overheating.

In general, the prior art of designing and manufacturing consumer appliances such as toasters, toaster ovens, coffee makers, and the like can be consulted to provide examples of how to incorporate wiring, switches, lights, timers, and thermostat devices into the present invention. Such designs and related manufacturing methods are considered generally well known in the art, and are not set forth in great detail herein.

While the present invention has been described in terms of a preferred embodiment, it is apparent that other forms could be adopted by one skilled in the art. For example, the teachings of the present invention are also well suited to test tube warmers, syringe warmers, and the like. Those skilled in the art will appreciate that other applications, including those outside of the neo-natal intensive care setting are possible with this invention. Accordingly, the present invention is not limited to only baby bottle heating devices, and the scope of the present invention is to be limited only by the following claims.

What is claimed is:

1. A heating device comprising:
   a heater block comprising at least one void therein;
   at least one removable reservoir disposed within said at least one void of said heater block; and
   means for heating said at least one removable reservoir, said means for heating being disposed between said at least one removable reservoir and said heater block within each said at least one void.

2. The heating device as claimed in claim 1, further comprising means for vibrating said heater block, said means for vibrating being in direct contact with said heater block.

3. The heating device as claimed in claim 2, wherein said vibrating means comprises a vibrating platform upon which said heater block is mounted.

4. The heating device as claimed in claim 1, wherein said means for heating comprises at least one resistor coil.

5. The heating device as claimed in claim 1, wherein said means for heating further comprises at least one rocker switch mounted to said heater block for controlling said means for heating.

6. The heating device as claimed in claim 1, wherein heater block further comprises at least one indicator light mounted thereto for signaling that said heater device has reached a desired stabilized temperature.

7. The heating device as claimed in claim 1, further comprising an automatic shutoff feature.

8. The heating device as claimed in claim 1, further comprising a dry erase marker surface on said heater block.

9. The heating device as claimed in claim 1, further comprising a thermostat device mounted to said heater block such that said heating device is capable of being set to a desired stabilized temperature.

10. A liquid container heating device for a liquid to a desired temperature, said liquid container heating device using heat exchange of a heating fluid with a container, said liquid container heating device comprising:

a heater block comprising at least one well therein;

at least one removable reservoir for receiving said heating fluid, said at least one removable reservoir being disposed within said at least well of said heater block; and at least one heating element for heating said heating fluid, said at least one heating element being disposed between said at least one removable reservoir and said at least one well of said heater block;

wherein said container is placed in said heating fluid, said at least one removable reservoir, said at least one heating element heats said at least one removable reservoir and said heating fluid, and said heating fluid in turn heats said container, whereby said liquid within said container rendered suitably heated for use.

11. The liquid container heating device as claimed in claim 10, wherein said at least one heating element comprises at least one resistor coil.

12. The liquid container heating device as claimed in claim 10, further comprising at least one rocker switch mounted to said heater block for controlling said at least one heating element.

13. The liquid container heating device as claimed in claim 10, wherein said heater block further comprises at least one indicator light mounted thereto for signaling that said liquid container heating device has reached a desired stabilized temperature.

14. The liquid container heating device as claimed in claim 10, further comprising a thermostat device mounted to said heater block such that said liquid container heating device is capable of being set to a desired stabilized temperature.

15. The liquid container heating device as claimed in claim 10, further comprising a dry erase marker surface on said heater block.

16. The liquid container heating device as claimed in claim 10, further comprising an automatic shutoff feature.

17. The liquid container heating device as claimed in claim 10, further comprising a vibrating device for vibrating said heater block, said vibrating device being in contact with said heater block.

18. A baby bottle heating device for controllably thawing and warming a frozen liquid contained in at least one baby bottle using heat transfer from a heating fluid, said baby bottle heating device comprising:

a heater block composed of heat insulative material, said heater block comprising at least one container well therein;

at least one sleeve disposed within said at least one container well;

at least one removable reservoir disposed within said at least one sleeve; and at least one heating element for heating said heating fluid, said at least one heating element being disposed between said at least one removable reservoir and said at least one sleeve;

whereby at least one heating element heats said at least one removable reservoir, heat transfers through said at least one removable reservoir and into said heating fluid contained therein, and heat transfer through said heating fluid and through said at least one baby bottle into said frozen liquid so as to render said frozen liquid suitably heated for administration to a newborn child.

\* \* \* \* \*

UNITED STATES PATENT AND TRADEMARK OFFICE
CERTIFICATE OF CORRECTION

PATENT NO.    : 6,417,498 B1
DATED         : July 9, 2001
INVENTOR(S)   : Janice M. Shields and Paul W. Shields It is certified that error appears in the above-identified patent and that said Letters Patent is hereby corrected as shown below:

<u>Title page,</u>
Item [74], kindly delete "Vanophem & Vanophem", and insert
-- VanOphem & VanOphem --.

<u>Column 1,</u>
Line 62, after "works", kindly delete the comma ",".

<u>Column 3,</u>
Line 24, after "that", kindly delete "when", and insert a comma -- , --.

<u>Column 5,</u>
Line 39, after "56", kindly insert -- is --.

<u>Column 7,</u>
Line 1, after "wherein", kindly insert -- said --.
Line 13, after "for", kindly insert -- heating --.
Line 20, after "least", kindly insert -- one --.
Line 26, after "fluid", kindly delete the comma "," and insert -- in --.
Line 30, after "container", kindly insert -- is --.

<u>Column 8,</u>
Line 33, after "whereby", kindly insert -- said --.
Line 36, kindly delete "transfer", and insert -- transfers --.

Signed and Sealed this

Eighth Day of April, 2003

JAMES E. ROGAN
*Director of the United States Patent and Trademark Office*